United States Patent [19]

Palsrok et al.

[11] Patent Number: 4,997,421
[45] Date of Patent: Mar. 5, 1991

[54] IV CONNECTOR LOCK AND STABILIZER

[75] Inventors: Gary Palsrok; Bonnie Palsrok, both of Manistee, Mich.

[73] Assignee: Dale Medical Products, Inc., Plainville, Mass.

[21] Appl. No.: 940,440

[22] Filed: Dec. 10, 1986

[51] Int. Cl.⁵ .............................................. A61M 5/32
[52] U.S. Cl. ................................... 604/174; 604/283; 128/DIG. 26
[58] Field of Search ........... 128/133, 334 C, DIG. 26; 604/165, 174–180, 283, 905; 285/61, 420, 114; 24/339, 346

[56] References Cited

U.S. PATENT DOCUMENTS

| | | | |
|---|---|---|---|
| 1,310,627 | 7/1919 | McEvilly | 285/114 |
| 3,479,069 | 11/1969 | Sedam | 285/420 |
| 3,702,612 | 11/1972 | Schlesinger | 128/DIG. 26 |
| 3,881,753 | 5/1975 | Bochory | 285/420 |
| 4,082,094 | 4/1978 | Dailey | 128/DIG. 26 |
| 4,224,937 | 9/1980 | Gordon | 128/DIG. 26 |
| 4,230,109 | 10/1980 | Geiss | 604/280 |
| 4,230,110 | 10/1980 | Beroff | 604/280 |
| 4,333,505 | 6/1982 | Jones et al. | 604/905 |
| 4,362,156 | 12/1982 | Feller, Jr. et al. | 604/177 |
| 4,397,647 | 8/1983 | Gordon | 128/DIG. 26 |
| 4,435,174 | 3/1984 | Redmond et al. | 604/174 |
| 4,563,177 | 1/1986 | Kamen | 128/DIG. 26 |

Primary Examiner—Stephen C. Pellegrino
Assistant Examiner—Ralph A. Lewis
Attorney, Agent, or Firm—Schiller, Pandiscio & Kusmer

[57] ABSTRACT

An IV lock for preventing IV connectors from separating. The IV lock has a split-fork lock at one end for releasably securing a male IV fitting or connector to the IV lock and a snap-fit clamp at the opposite end for releasably securing a catheter to the IV lock. The male IV fitting and catheter are prevented from moving axially and transversely of their length when secured in the IV lock. The IV lock supports the IV fitting and catheter at the same angle at which the catheter was inserted into the patient. Apertures are provided in the base of the IV lock so that IV fluid flowing through the male IV fitting may be viewed against the skin of the patient.

4 Claims, 1 Drawing Sheet

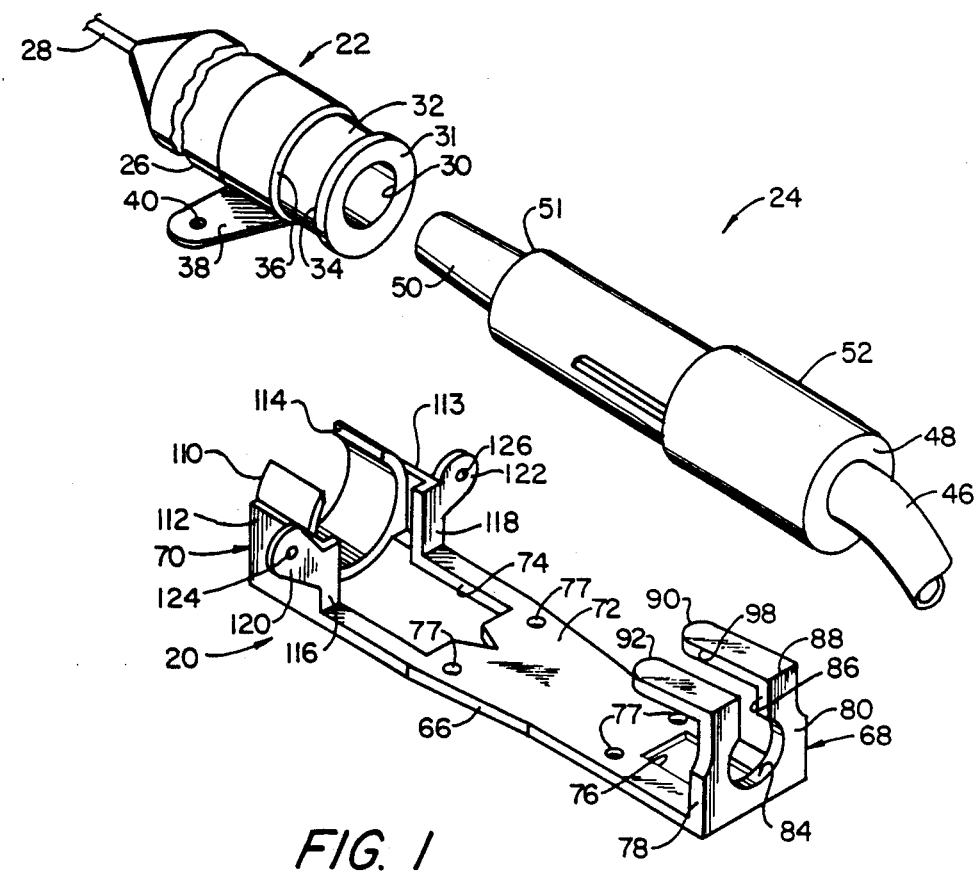
FIG. 1
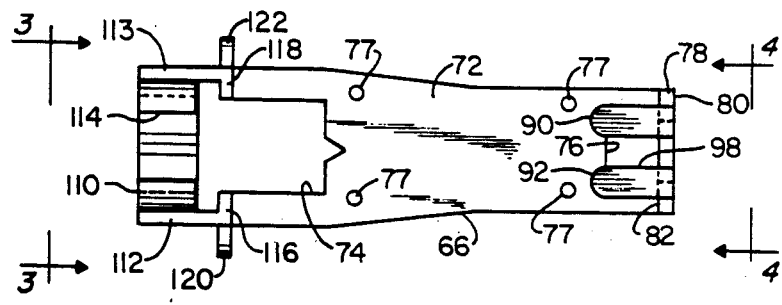
FIG. 2
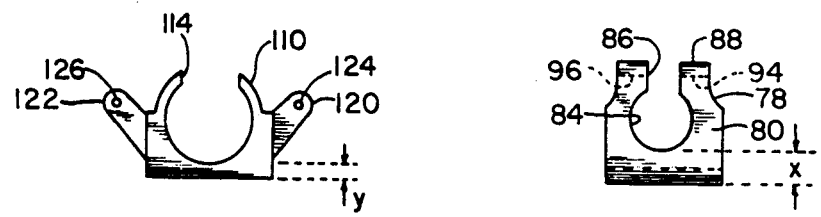
FIG. 3
FIG. 4

IV CONNECTOR LOCK AND STABILIZER

This invention relates to medical apparatus used in administering intravenous fluid to a patient, and more particularly to a bracket for securing a male intravenous fitting to a female intravenous catheter.

As is well known by health care professionals and others associated with the health care field, intravenous (hereinafter "IV") fluid is typically administered through a catheter inserted into a vein. The catheter is coupled to a male IV fitting which is connected by IV tubing to a supply of IV fluid. Not infrequently, the male IV fitting becomes separated from the catheter, often causing leakage of intravenous fluid and blood. Separated IV lines may also cause hemorrhaging in the patient and may provide a site from which infectious germs and other contaminants may enter the patient's body. Air may also enter the patient's circulatory system when the connection between the male IV fitting and catheter is broken. If an embolism develops in the patient's circulatory system due to this introduction of air, cardiac damage, paralysis, coma or even death may result.

In addition to the problems set forth above, a disconnected IV tube often creates additional work for health care personnel. For instance, it typically takes ten to fifteen minutes to change a leaky IV connection and five to ten minutes to replace IV fluid-soaked bed sheets.

Several methods of, and apparatus for, securing a male IV fitting to an IV catheter have been developed. In one known method, after the catheter has been inserted in the patient's vein, the male IV fitting is inserted in the catheter so as to frictionally engage the latter in a manner establishing a fluid-tight seal between the male IV fitting and the catheter. Then the entire assembly is bonded by adhesive tape and is secured to the patient, also by adhesive tape. This procedure is relatively slow and does not couple the catheter to the male IV fitting as securely as may be desired. Alternatively, IV connection locks such as those marketed under the trademark Luer Lock or such as those described in U.S. Pat. No. 4224937 have been used to secure male IV fittings to catheters. Luer Lock-type IV connector locks have been known to torque the cannula in a manner causing skin breakdown. Also, Luer Lock-type connectors on occasion are softened by the patient's body temperature resulting in leakage at the point of sealing between the male IV fitting and the catheter. The IV connector lock of U.S. Pat. No. 4224937 is designed to lock the male IV connector, in part, by friction grip, with the result that if the male IV connector is pulled away from the catheter with sufficient force to overcome the friction grip, the male IV fitting may tend to separate from the catheter resulting in leakage of IV fluid. Another disadvantage of certain known IV connector locks is that they are designed to receive the catheter and male IV fitting of only one specific type of IV system. Other known IV connector locks suffer from the disadvantage of being relatively expensive.

The primary object of the present invention is to overcome the disadvantages and problems of known IV connector locks set forth above.

Another primary object of the present invention is to provide IV connector lock for coupling a male IV fitting to a catheter in a manner substantially eliminating the possibility of the fitting becoming inadvertently fluidly decoupled from the catheter.

Other objects of the invention include providing an IV connector lock that (1) fits smoothly on the patient's skin in a manner avoiding the application of pressure which might injure the patient's skin, (2) fits a variety of IV systems, (3) supports the catheter at the same angle at which it was inserted into the patient, (4) permits the male IV fitting to be connected to and disconnected from the catheter without causing discomfort to the patient and (5) locks both the male IV fitting and the catheter, when secured together, to the IV connector lock.

Other objects of the invention will in part be obvious and will in part appear hereinafter. The invention accordingly comprises the product possessing the features, properties and relation of components described hereinafter, and the scope of the application of which will be indicated in the claims.

The IV connector lock and stabilizer of the present invention comprises a bracket having a base, a first lock mounted to one end of the base for releasably gripping a conventional male IV fitting, and a second lock mounted to the opposite end of the base for releasably gripping a conventional IV catheter fluidly coupled to said male IV fitting. Apertures are provided in the base to permit viewing against the patient's skin of the IV fluid flowing through the male IV fitting. The catheter is supported by the bracket of the invention at the same angle with respect to the patient's skin at which it is inserted in the patient.

For a fuller understanding of the nature and objects of the present invention, reference should be had to the following detailed description taken in connection with the accompanying drawings wherein:

FIG. 1 is an isometric view of the IV connector bracket of the present invention shown together with the conventional male IV fitting and a portion of the conventional catheter which the bracket is adapted to secure together;

FIG. 2 is a plan view of the bracket of the invention;

FIG. 3 is an end view of the bracket taken along line 3—3 in FIG. 2; and

FIG. 4 is an end view of the bracket taken along line 4—4 in FIG. 2.

Referring to FIG. 1, the present invention is an IV connection lock and stabilizer ("IV lock") 20 for ensuring catheter 22 remains fluidly coupled to male IV fitting 24. Catheter 22 and IV fitting 24 are used with the present invention, but do not constitute part of the invention.

Catheter 22 is a conventional catheter used to administer intravenous fluid to a patient. Catheter 22 is hollow and comprises hub 26 and sheath 28 fluidly connected to the front end of the hub. The interior of hub 26 tapers conically outwardly toward aperture 30 formed in rear end 31 of the hub. An annular portion 32 is formed in the outer surface of hub 26 adjacent rear end 31. Portion 32 is flanked by upstanding shoulders 34 and 36. A pair of flanges 38 (only one of which is shown in FIG. 1) are secured to the outer surface of hub 26. An aperture 40 is formed in each flange for use in suturing the flange and attached catheter to the skin of a patient.

Although catheters of the type identified at 22 are produced by a variety of manufacturers, such as Abbott Laboratories of Abbott Park, Ill., certain portions of the catheter are made by most of the various manufacturers to standard dimensions. For instance, the outside diameter of annular portion 32 and the axial distance between shoulders 34 and 36 is typically standardized, as is the diameter and taper of the hollow interior of hub 26.

Male IV fitting 24 is also a conventional fitting of the type manufactured by Abbott Laboratories and others. Fitting 24 is translucent and hollow. A hollow frusto-conically tapering front portion 50 is secured to the front end 51 of fitting 24. The outside diameter and taper of front portion 50 are selected so that when inserted in aperture 30, front portion 50 will form a fluid-tight, friction fit with the interior of hub 26. IV tube 46 is fluidly connected to fitting 24 at its rear end 48. IV tube 46 usually has an outside diameter in the range of from 0.210" to 0.260" and is available from a variety of manufacturers, such as Abbott Laboratories. Rear portion 52 of fitting 24 is formed so that the outside diameter of the former is radially spaced a selected distance from the outside diameter of IV tube 46.

As with catheter 22, certain portions of IV fiting 24 are made to standard dimensions by most manufacturers. For instance, the radial spacing between IV tube 46 and the outer surface of rear portion 52 is typically standardized, as is the distance between rear end 48 and front end 51, as measured along the length of the fitting.

IV lock 20, as illustrated in FIGS. 1, 2 and 4, comprises base 66, split-fork lock 68 and snap-fit clamp 70. IV lock 20 is preferably made from a material that is relatively rigid while also being slightly resilient, such as polystyrene. Known molding procedures, such as hot-air injection molding, may be satisfactorily employed in the fabrication of IV lock 20.

Base 66 comprises substantially flat top surface 72 and an opposing substantially flat bottom surface (not shown). Base 66 has a thickness sufficient to ensure that the base remains substantially inflexible over its length. The length of base 66 corresponds to the distance between shoulder 36 and rear end 48 when IV clamp 24 is fluidly coupled to catheter 22, as described more fully below. Apertures 74 and 76 are formed in base 66 at opposite ends thereof and extend entirely through the latter. A plurality of small apertures 77 are formed in base 66 for use in suturing IV lock 20 to the skin of the patient.

Split-fork lock 68 is secured to base 66 adjacent aperture 76. Lock 68 comprises base portion 78, the latter having opposed, parallel, flat surface 80 and 82 (FIG. 2) formed thereon. Surfaces 80 and 82 form an approximately 90° angle with respect to top surface 72. Aperture 84 and slot 86 are formed extending entirely through base portion 78. Slot 86 is connected to aperture 84 so that the aperture opens upwardly toward top edge 88 of portion 68. The diameter of aperture 84 is substantially identical to the outside diameter of IV tube 46 and the width of slot 86 is slightly less than the outside diameter of IV tube 46. The base of aperture 84 is spaced a distance x (FIG. 4) from the bottom surface of base portion 66.

Fingers 90 and 92 are coupled to base portion 78 at top edge 88 on opposite sides of slot 86 and extend toward the opposite end base 66 in which aperture 74 is formed. Fingers 90 and 92 have flat underside surfaces 94 (FIG. 4) and 96 (FIG. 4) which form an acute angle with surfaces 80 and 82 that ranges between 81 and 87 degrees, with 84 degrees being the preferred angle. The vertical distance between the center of aperture 84 and the underside surfaces 94 and 96 where they join surface 82 is substantially identical to the radial spacing between the center of IV tube 46 and the outer surface of rear portion 52. Slot 98 extends between fingers 90 and 92 and is coupled to slot 86 and has the same width as slot 86.

Turning now to FIGS. 1–4, snap-fit clamp 70 comprises cylinder 110 secured via sidewalls 112 and 113 to base 66 adjacent aperture 74. The inside diameter and axial length of cylinder 110 are substantially identical to the outside diameter and axial length of annular portion 32. Cylinder 110 is secured to base 66 so that its longitudinal axis forms an angle ranging from 4 to 8 degrees with the long dimension of top surface 72, 6 degrees being the preferred angle. An opening 114 is formed in the top portion of ring 110. Opening 114 spans an approximately 90 degree segment of the circumference of ring 110. The bottommost portion of the interior of cylinder 110 is spaced a distance y (FIG. 3) from the bottom surface of base 66. As described more fully below, distance y is less than distance x (FIG. 4).

A pair of vertically extending walls 116 and 118 are secured to base 66 and sidewalls 112 and 113, respectively, adjacent aperture 74 between cylinder 110 and split fork lock 68. Walls 116 and 118 are spaced from cylinder 110 along the length of base 66 a distance slightly greater than the axial spacing between shoulder 34 and end 31. A pair of laterally-extending brackets 120 and 122 are secured, respectively, to walls 116 and 118. Apertures 124 and 126 are formed in brackets 120 and 122 respectively, for use in suturing the brackets and IV lock 20 to the skin of a patient.

The present invention is used in the following manner for securing a catheter inserted in a patient to an IV fitting adapted for attachment to a source of intravenous fluid. After preparing the venipuncture site, catheter sheath 28 is inserted into a vein using conventional venipuncture techniques. Front portion 50 is then inserted in aperture 30 until a fluid-tight seal is achieved between portion 50 and the interior of hub 26. When coupled together in this manner, intravenous fluid flows from the source thereof through IV tube 46, fitting 24, hub 26 and sheath 28 and into the patient. Next, IV tube 46 is forced through slots 86 and 98 until the IV tube is received in aperture 84. Since the outside diameter of tube 46 is slightly greater than the width of slots 86 and 98, the IV tube flattens slightly as it is forced through the slots. Coupled fitting 24 and catheter 22 are then moved axially until rear portion 48 engages surface 82. In this position the outer surface of rear portion 52 engages the underside surfaces 94 and 96 of fingers 90 and 92, respectively, due to the vertical placement of aperture 84 on portion 78. Annular portion 32 is then urged through opening 114 into cylinder 110. IV lock 20 is made from a slightly resilient material so that the walls of cylinder 110 adjacent opening 114 will spread apart slightly as annular portion 32 is forced through the opening. When annular portion 32 is received in cylinder 110, the inner surface of cylinder 110 engages the outer surface of annular portion 32 so as to releasably secure the latter in cylinder 110. When annular portion 32 is secured in this manner, shoulder 34 and end 31 are received in the space between cylinder 110 and walls 116 and 118. Finally, if desired, IV lock 20 may be sutured to the skin of the patient using apertures 77 and 124. In some cases it may be desirable to suture IV lock 20 to the patient prior to securing catheter 22 and fitting 24 in the lock.

As noted above, the base of aperture 84 is spaced distance x from the bottom of base 66 and the base of the interior of cylinder 110 is spaced distance y from the bottom of base 66. Distance x is greater than distance y with the result that the catheter 22 fitting and sheath 28 are supported at the same angle with respect to the patient's skin at which sheath 28 was inserted into the patient. Typically, this angle is about 6 degrees. Fingers 90 and 92 are also inclined about 6 degrees toward base 66 and cylinder 110 is inclined away about 6 degrees from base 66. Thus, substantially the entire length of the underneath surfaces 94 and 96 of fingers 90 and 92 engage the outer surface of rear portion 52 of fitting 24 and surface 82 of lock 68 engages rear end 48 of fitting 24. By this engagement, fitting 24 is prevented from moving transversely of its length.

Catheter 22 is similarly prevented from moving transversely of its length when secured in cylinder 110. Under normal conditions, the walls of cylinder 110 adjacent opening 114 prevent hub 26 from escaping from the cylinder through opening 114. When it is desired to remove catheter 22 from IV lock 20, the hub may be pulled through opening 114 with sufficient force to deform the walls of cylinder 110 adjacent the opening. Typically, the force required to remove catheter 22 from IV lock 20 is greater than the force a patient might accidentally exert on the catheter.

Catheter 22 and fitting 24 are also prevented from moving axially relative to one another and relative to the venipuncture site when secured in IV lock 20. As noted above, with conventional IV fittings, when catheter 22 is coupled to fitting 24 the distance between ends 31 and 48 is standardized. The length of base 66 is selected so that the distance between base portion 78 and cylinder 110 corresponds to this standardized distance. Consequently, when catheter 22 and fitting 24 are secured in IV lock 20, rear end 48 engages surface 82, shoulders 34 and 36 engage cylinder 110 and end 31 engages walls 116 and 118. In this position the coupled catheter 22 and fitting 24 are prevented from moving axially.

Apertures 74 and 76 are provided to facilitate the observation of IV fluid flowing through translucent fitting 24. By looking downwardly onto the fitting 24, the intravenous fluid flowing through the fitting is visible against the relatively dark skin of the patient exposed through apertures 74 and 76.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A bracket for supporting and for preventing separation and leakage between an elongate, hollow intravenous fitting fluidly coupled to an elongate, hollow catheter, the fitting having a shoulder and the catheter having a shoulder, said bracket comprising:
   a base having a first end and a second end;
   a first clamp means mounted to said first end of said base for releasably locking said intravenous fitting to said base so that said intravenous fitting is restrained from moving transversely relative to its length, and for engaging said fitting shoulder so as to restrain positively said fitting from moving axially in a first direction along its length away from said second end of said base; and
   second clamp means mounted to said second end of said base for releasably locking said catheter to said base so that said catheter is restrained from moving transversely relative to its length, and for engaging said catheter shoulder so as to restrain positively said catheter from moving axially along its length away from said first end in a direction opposite said first direction,
   wherein said base includes a substantially flat surface, and said first clamp means comprises:
   a first member attached at its bottom end to said first end of said base, said first member having a substantially flat inner surface extending so as to form an angle of approximately 90 degrees with respect to said substantially flat surface of said base, said first member having a top end opposite said bottom end;
   an aperture extending through said first member;
   a slot extending through said first member coupled with said aperture so as to split said first member into first and second sections, said slot intersecting said top end of said first member;
   first and second fingers attached, respectively, to said first and second sections so as to extend toward said second end of said base, said first and second sections each having an intravenous fitting-engaging surface for engaging said fitting shoulder, which surfaces form an acute angle of between about 82 to 86 degrees with respect to said inner surface of said first member; and
   a slot extending between said first and second fingers coupled with said slot in said first member.

2. A bracket for supporting and for preventing separation and leakage between an elongate, hollow intravenous fitting fluidly coupled to an elongate, hollow catheter, the fitting having a shoulder and the catheter having a shoulder, said bracket comprising:
   a base having a first end and a second end;
   a first clamp means mounted to said first end of said base for releasably locking said intravenous fitting to said base so that said intravenous fitting is restrained from moving transversely relative to its length, and for engaging said fitting shoulder so as to restrain positively said fitting from moving axially in a first direction along its length away from said second end of said base; and
   second clamp means mounted to said second end of said base for releasably locking said catheter to said base so that said catheter is restrained from moving transversely relative to its length, and for engaging said catheter shoulder so as to restrain positively said catheter from moving axially along its length away from said first end in a direction opposite said first direction, said intravenous fitting being made of a substantially transparent material, said base comprising at least one aperture extending therethrough so that when said bracket contacts the skin of a patient, the flow of intravenous fluid through the intravenous tube connector may be viewed against the skin of the patient through said aperture.

3. A bracket for preventing separation and leakage between an elongate, hollow intravenous fitting fluidly coupled to an elongate, hollow catheter, said bracket comprising:
   a base having a substantially flat elongate surface for engaging the skin of a patient;
   at least one aperture extending through said base;
   a first member attached at its bottom end to one end of said base, said first member having a substantially flat inner surface extending so as to form a right angle with respect to said substantially flat surface of said base, said first member having a top end opposite said bottom end;

an aperture extending through said first member;

a slot extending through said first member coupled with said aperture so as to split said first member into first and second sections, said slot intersecting said top end of said first member, first and second fingers attached, respectively, to said first and second sections so as to extend toward an opposite end of said base, said first and second sections each having an intravenous fitting-engaging surface which forms an angle of between about 82 to 86 degrees with respect to said inner surface of said first member;

a slot extending between said first and second fingers coupled with said slot in said first member;

a cylindrical member attached to said opposite end of said base so that the longitudinal axis of said cylindrical member forms an angle with the long dimension of said substantially flat elongate surface, a top portion of said cylindrical member spanning approximately 25% of the entire circumference of said cylindrical member being removed, said cylindrical member being formed of a relatively resilient material; and a wall portion secured to said base adjacent said cylindrical member between said cylindrical member and said first member, said wall portion having a substantially flat surface extending substantially normally to said substantially flat surface of said base, said wall having an aperture formed therein separating said wall into first and second halves.

4. A bracket for preventing separation and leakage between an elongate hollow intravenous fitting fluidly coupled to an elongate, hollow catheter, said bracket comprising:

a base;

lock means mounted on said base and including first clamp means for releasably locking said intravenous fitting to said base, and second clamp means for releasably locking said catheter to said base, so as to prevent and intravenous fitting from separating from said catheter and leaking fluid present in the interior of the intravenous fitting or catheter, further wherein:

said first clamp means is mounted to one end of said base for releasably locking said intravenous fitting to said base so that said intravenous fitting is restrained from moving transversely relative to its length and axially in a first direction along its length, and first clamp means further comprising:

a first member attached at its bottom end to said one end of said base, said first member having a substantially flat inner surface extending so as to form an angle of approximately 90 degrees with respect to said substantially flat surface of said base, said first member having a top end opposite said bottom end;

an aperture extending through said first member;

a slot extending through said first member coupled with said aperture so as to split said first member into first and second sections, said slot intersecting said top end of said first member;

first and second fingers attached, respectively, to said first and second sections so as to extend toward an opposite end of said base, said first and second sections each having an intravenous fitting-engaging surface which forms an acute angle of between about 82 to 86 degrees with respect to said inner surface of said first member;

a slot extending between said first and second fingers coupled with said slot in said first member; and said second clamp means is mounted to said opposite end of said base for releasably locking said catheter to said base so that said catheter is restrained from moving axially or transversely relative to its length, said second clamp means cooperating with said first clamp means so as to prevent said intravenous fitting from moving in a second direction along its length.

* * * * *

UNITED STATES PATENT AND TRADEMARK OFFICE
CERTIFICATE OF CORRECTION

PATENT NO. : 4997421

DATED : March 5, 1991

INVENTOR(S) : Gary Palsrok, et al.

It is certified that error appears in the above-identified patent and that said Letters Patent is hereby corrected as shown below:

Claim 4, column 8, line 1, delete "and" and substitute therefor --said--.

Signed and Sealed this

Fourth Day of August, 1992

Attest:

DOUGLAS B. COMER

Attesting Officer

Acting Commissioner of Patents and Trademarks